United States Patent [19]

Simmons

[11] Plant 4,793

[45] Nov. 24, 1981

[54] SPUR TYPE RED ROME APPLE TREE—PEACH VALLEY CULTIVAR

[75] Inventor: Dan E. Simmons, Rogers, Ohio

[73] Assignee: Stark Brothers Nurseries & Orchards Co., Louisiana, Mo.

[21] Appl. No.: 151,248

[22] Filed: May 19, 1980

[51] Int. Cl.[3] ..... A01H 5/03

[52] U.S. Cl. ..... Plt./34

[58] Field of Search ..... Plt./34

*Primary Examiner*—Robert E. Bagwill

*Attorney, Agent, or Firm*—Burns, Doane, Swecker & Mathis

[57] ABSTRACT

A new and distinct apple variety which originated as a limb mutation of the Law cultivar of the Red Rome apple tree (i.e. U.S. Plant Pat. No. 1,550) is provided. This new apple variety possesses a vigorous compact growth habit and can be distinguished from its standard sized parent and all other spur type Red Rome apple varieties. More specifically, the new variety possesses more fruiting spurs per linear foot on one, two, and three year old wood than both its parent and the spur type Red Rome apple tree of U.S. Plant Pat. No. 4,096 which also was originated by me. Additionally, the fruit of the new variety is a deeper, more intense and complete red which accumulates earlier than that of the Taylor cultivar of the Red Rome apple tree (i.e. U.S. Plant Pat. No. 3,121) and the Red Rome apple tree of U.S. Plant Pat. No. 3,198.

2 Drawing Figures

SUMMARY OF THE INVENTION

The new and distinct variety first came to my attention during December, 1976 while growing as a limb mutation in the cultivated Peace Valley Orchards (Dan Simmons farm) at Rogers, Ohio 44455. More specifically, the limb mutation was discovered on a six year old tree of the Law Cultivar of Red Rome apple growing on MM-106 rootstock in Block No. 3 of such orchards. The parent tree had been originally obtained from the Stark Brothers Nurseries & Orchards Company.

I was originally attracted to the limb mutation by its vigorous compact growth habit whereby heavy quantities of spurs are present. Continued observation and testing over a number of years has indicated that this discovery is in fact a new and distinct variety which differs from all previously known Red Rome apple varieties of which I am aware.

The new variety of apple tree possesses the following combination of characteristics:

(a) a vigorous compact growth habit, (b) large deep green leaves, (c) the ability to bear fruit which is a deeper more intense red color accumulated earlier than that of the Taylor cultivar of Red Rome apple tree (U.S. Plant Pat. No. 3,121) and the Red Rome apple tree of U.S. Plant Pat. No. 3,198, (d) the ability to form substantially more fruiting spurs on one year old shoots than the Red Rome apple of U.S. Plant Pat. No. 4,096, and (e) the ability to form more fruiting spurs on two and three year old wood than the Red Rome apple of U.S. Plant Pat. No. 4,096.

More specifically, it has been found that the Red Rome apple tree of U.S. Plant Pat. No. 4,096 forms few if any fruiting spurs on one year old shoots. On the contrary the present variety forms many fruiting spurs on such one year old shoots. Accordingly, the present variety is expected to begin fruit production at an earlier age if good horticultural practices are followed.

Also, the characteristics of two and three year old wood of the new variety were compared in detail with those of the Red Rome apple tree of U.S. Plant Pat. No. 4,096 while growing at Rogers, Ohio. On such two year old wood it was found that the distance between fruiting spurs for the new variety averaged approximately 6.2 inches while the distance for the Red Rome apple tree of U.S. Plant Pat. No. 4,096 averaged approximately 8.2 inches. The three year old wood of the present variety possessed a substantial number of fruiting spurs while the Red Rome apple tree of U.S. Plant Pat. No. 4,096 commonly possessed barren areas, sometimes referred to as blindwood.

The fruit of the new variety is substantially identical in size, shape, and color to that of the law Cultivar of Red Rome apple tree (i.e. U.S. Plant Pat. No. 1,550) and the Red Rome apple tree of U.S. Plant Pat. No. 4,096. Additionally, the blossom dates and appearance are substantially identical to those of the Law Cultivar of Red Rome apple tree and the Red Rome apple tree of U.S. Plant Pat. No. 4,096. The dates of first and last fruit pickings are substantially identical to those of the Law Cultivar of Red Rome apple tree.

Asexual propagation at Rogers, Ohio over a number of years now has demonstrated that the unique combination of characteristics of this new variety comes true to form and is established and transmitted through succeeding propagations.

All specimens described herein were grown and observed at Rogers, Ohio.

The new variety has been named the Peace Valley cultivar.

BRIEF DESCRIPTION OF THE PHOTOGRAPHS

The photographs were obtained during October, 1979 at Rogers, Ohio, and are presented in color as true as reasonably possible in an illustration of this character.

Plant Pat. No. 4,096 wherein spurs are substantially absent on one year old wood and relatively long side shoots are present on two year old wood together with less numerous fruiting spurs.

Figure 1:
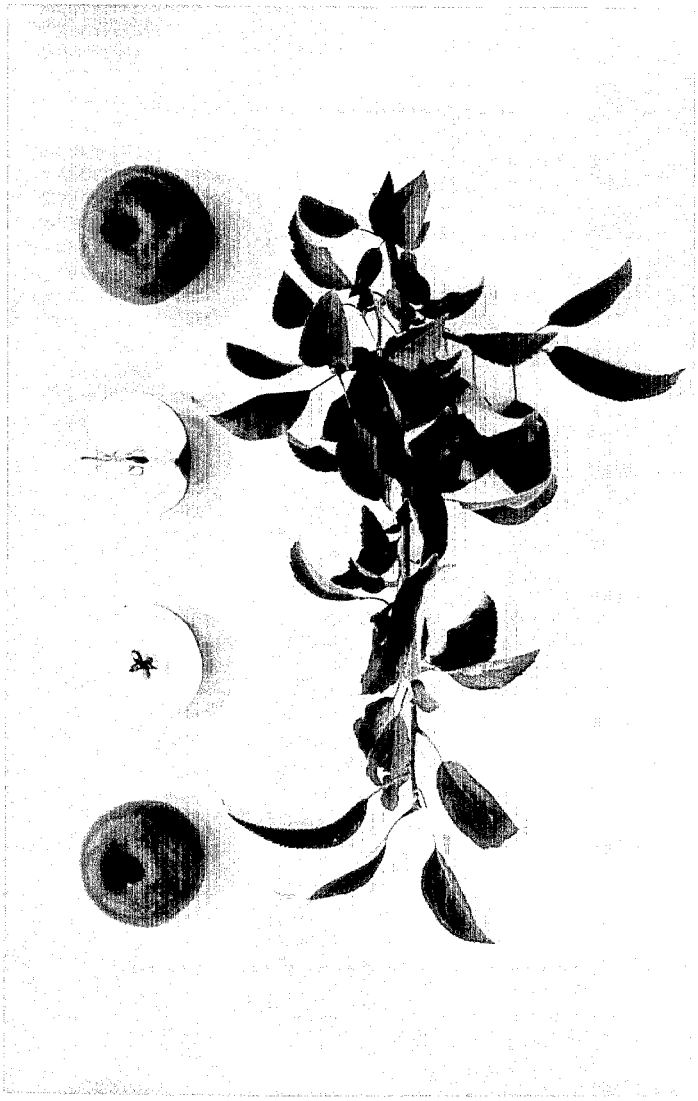
FIG. 1 shows typical specimens of the fruit and foliage of the new variety.
Figures 2, 3, 4:
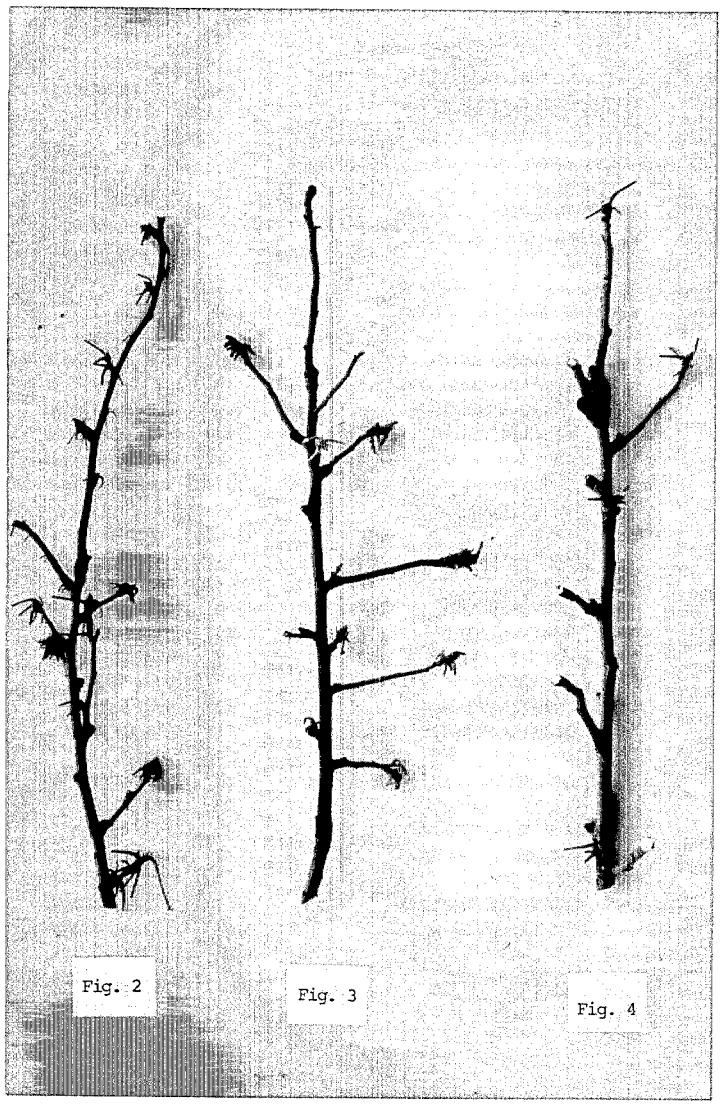
FIG. 2 shows a typical defoliated shoot of one and two year old wood of the new variety which illustrates the numerous presence of fruiting spurs.
FIG. 3 shows a typical defoliated shoot of one and two year old wood of the Red Rome apple tree of U.S.

FIG. 4 shows a typical defoliated shoot of one and two year old wood of the Law Cultivar of Red Rome apple tree (U.S. Plant Pat. No. 1,550) wherein fruiting spurs are substantially absent on one year old wood and are substantially less numerous on two year old wood. Relatively long side shoots have been cut back.

DETAILED DESCRIPTION OF THE NEW VARIETY

The following is a detailed description of my new variety where color terminology is to be accorded its ordinary dictionary significance except where otherwise indicated. The specimens described were grown at Rogers, Ohio.

Dates of first and last pickings — October 10 and 15 in Ohio; the fruit commonly ripens at the same time as the Law Cultivar of Red Rome apple tree.

Tree: Small; vigorous; slightly drooping but compact; dense; round-topped; slow growing; hardy; very productive; regular bearing.

*Trunk.*—Smooth; grey.

*Lenticels.*—Few to medium.

*Leaves.*—Medium long; ovate; taper-pointed; length — approximately 3 to 3¾ inches; width — approximately 1¼ to 2 inches.

*Petiole.*—Length — approximately 1¼ to 1½ inches; medium; slender.

Flowers: Date of first bloom — May 15, 1978; date of full bloom — May 18, 1978; white; substantially identical to those of the Law Cultivar of Red Rome apple tree and the Red Rome apple tree of U.S. Plant Pat. No. 4,096.

Fruit: Maturity when eating ripe — approximately October 15.

*Size.*—Uniform-variable; axial diameter — approximately 2⅝ to 3 inches; globose-oblate.

*Cavity.*—Symmetrical; flaring toward apex; even; pubescent toward apex; depth — approximately 5/16 inch; breadth — approximately 1⅛ inch.

*Basin.*—Symmetrical; rounded; pubescent; depth — approximately 1¼ inch; breadth — approximately ¾ to 1 inch; markings — none.

*Stem.*—Medium; length — approximately ¾ inch; breadth — approximately ⅛ inch.

*Color.*—Greenish red.

*Calyx.*—Open; decidious; narrowly lanceolate; acute; ascending; converged from base toward center; length — approximately 2/16 inch.

*Eye.*—Medium; partially closed.

*Skin.*—Thick; tough; rough; glossy; waxed; even to raised. Color of dots — white. Distribution of dots — plentiful; mottled; blushed. Ground color — Bright Carmine Plate 1 — Color No. 1 Tone i of Ridgeway Color Standards and Nomenclature. Bloom — moderate; white. General color effect — 100 percent red at maturity.

*Flesh.*—Rather juicy. Color — Satiny white with greenish tint. Texture — firm; fine and crisp. Flavor — mild.

*Core.*—Medium; distant in cross section. Bundle area (longitudinal section) — medium size; cordate; symmetrical; acute at base. Alternate bundle — core lines just clasping. Calyx tube — pubescent toward base; broadly obconic; entire depth — approximatey 5/16 inch. Styles — present; fleshy at base; united toward base; pubescent; glabrous toward base at apex. Stamens — in distinct whorl. Auxiliary cavity — present. Seed cells — axile; open; cell walls — distant; thick; tough; length — approximately ¾ inch; breadth — approximately ⅜ inch; longitudinal section — semi-orbicular; marginate; surface — fissured; smooth; cross section — broad.

*Seeds.*—Number perfect — 8; number imperfect — 1. Number in one cell — 2; length — approximately ⅜ inch. Breadth — approximately 3/16 inch. Form — acute. Color — Sorghum Brown Plate XXXIX — Color 9″ Tone i of Ridgeway Color Standards and Nomenclature.

Use: Market; dessert; culinary.

Keeping quality: Good — number of days in ordinary storage — 120 days.

I claim:

1. A new and distinct variety of apple tree substantially as illustrated and described characterized by (a) a vigorous compact growth habit, (b) large deep green leaves, (c) the ability to bear fruit which is a deeper more intense red color accumulated earlier than that of the Taylor cultivar of Red Rome apple tree described in U.S. Plant Pat. No. 3,121 and the Red Rome apple tree described in U.S. Plant Pat. No. 3,198, (d) the ability to form substantially more fruiting spurs on one year old shoots than the Red Rome apple tree described in U.S. Plant Pat. No. 4,096, and (e) the ability to form more fruiting spurs on two and three year old wood than the Red Rome apple tree described in U.S. Plant Pat. No. 4,096.

* * * * *

UNITED STATES PATENT AND TRADEMARK OFFICE

CERTIFICATE OF CORRECTION

PATENT NO. : PP 4793

DATED : November 24, 1981

INVENTOR(S) : Dan E. Simmons

It is certified that error appears in the above—identified patent and that said Letters Patent is hereby corrected as shown below:

Delete the present title and insert

--SPUR TYPE RED ROME APPLE TREE - PEACE VALLEY CULTIVAR--

Signed and Sealed this

Ninth Day of February 1982

[SEAL]

*Attest:*

GERALD J. MOSSINGHOFF

*Attesting Officer*

*Commissioner of Patents and Trademarks*